US007011953B2

(12) United States Patent
Abdelouahed et al.

(10) Patent No.: US 7,011,953 B2
(45) Date of Patent: Mar. 14, 2006

(54) DIAGNOSTIC ASSAY FOR TYPE 2 HEPARIN-INDUCED THROMBOCYTOPENIA

(76) Inventors: Mustapha Abdelouahed, 59 Alvarado Ave., #2, Worcester, MA (US) 01604; John W. Lawler, 6 Gale Rd., Swampscott, MA (US) 01907

(*) Notice: Subject to any disclaimer, the term of this patent is extended or adjusted under 35 U.S.C. 154(b) by 219 days.

(21) Appl. No.: 10/084,832

(22) Filed: Feb. 27, 2002

(65) Prior Publication Data
US 2002/0197697 A1    Dec. 26, 2002

Related U.S. Application Data

(63) Continuation of application No. PCT/US00/23707, filed on Aug. 29, 2000.

(60) Provisional application No. 60/151,314, filed on Aug. 30, 1999.

(51) Int. Cl.
G01N 22/567    (2006.01)

(52) U.S. Cl. .................. 435/7.21; 435/13; 436/518; 514/54; 514/56; 536/21

(58) Field of Classification Search .......... 435/7.21, 435/13; 514/54, 56; 536/21; 436/518
See application file for complete search history.

(56) References Cited

U.S. PATENT DOCUMENTS

| | | | | |
|---|---|---|---|---|
| 4,281,061 A | * | 7/1981 | Zuk et al. | 435/188 |
| 4,444,879 A | * | 4/1984 | Foster et al. | 435/7.95 |
| 5,466,582 A | * | 11/1995 | Amiral | 435/7.9 |
| 5,585,243 A | | 12/1996 | Aster et al. | |
| 5,763,201 A | * | 6/1998 | Tomer | 435/7.21 |
| 6,312,694 B1 | * | 11/2001 | Thorpe et al. | 424/178.1 |

FOREIGN PATENT DOCUMENTS

WO    WO 97/32211    9/1997

OTHER PUBLICATIONS

Guo et al, Heparin-binding Peptides from the Type I Repeats of Thrombospondin, 1992, The Journal of Biological Chemistry, vol. 267, No. 27, Issue of Sep. 25, pp. 19349-19355.*
Gogstad et al, British Journal of Haematology (England) Apr. 1983, vol. 53, No. 4, pp. 563-573 (Abstract Provided).*
Amiral, J., et al., "Antibodies to Macromolecular Platelet Factor 4-Heparin Complexes in Heparin-Induced Thrombocytopenia: a Study of 44 Cases," *Thrombosis and Haemostasis*, 73(1):21-28, (1995).
Amiral, J., et al., "Pathogenicity of IgA And/or IgM Antibodies to Heparin-PF4 Complexes in Patients with Heparin-Induced Thrombocytopenia," *British Journal of Haematology*, 92:954-959, (1996).
Amiral, J., et al., "Generation of Antibodies to Heparin-PF4 Complexes Without Thrombocytopenia in Patients Treated With Unfractionated or Low-Molecular-Weight Heparin," *American Journal of Hematology*, 52:90-95, (1996).
Griffiths, E. and Dzik, W.H., "Assays for Heparin-Induced Thrombocytopenia," *Transfusion Medicine*, 7:1-11, (1997).

(Continued)

Primary Examiner—Long V. Le
Assistant Examiner—Deborah A. Davis
(74) Attorney, Agent, or Firm—Hamilton, Brook, Smith & Reynolds, P.C.

(57) ABSTRACT

Methods for detecting the presence of antibodies to PF4/heparin/TSP-1 complexes in a biological sample and for diagnosing Type 2 heparin-induced thrombocytopenia are described.

2 Claims, 8 Drawing Sheets

OTHER PUBLICATIONS

Horne, M.K. III, and Hutchison K.J., "Simultaneous Binding of Heparin and Platelet Factor-4 to Platelets: Further Insights Into the Mechanism of Heparin-Induced Thrombocytopenia," *American Journal of Hematology*, 58:24-30, (1998).

Newman P.M., et al., "Heparin-Induced Thrombocytopenia: IgC Binding to PF4-Heparin Complexes in the Fluid Phase and Cross-Reactivity with Low Molecular Weight Heparin and Heparinoid," *Thromb Haemost.* 82:157-158, (1999).

Suh J.S., et al., "Antibodies from Patients with Heparin-Induced Thrombocytopenia/Thrombosis Recognize Different Epitopes on Heparin: Platelet Factor 4," *Blood* 91(3): 916-922, (1998).

Stringer, S.E. and Gallagher, J.T., "Specific Binding of the Chemokine Platelet Factor 4 to Heparan Sulfate," *The Journal of Biological Chemistry*, 272(33):20508-20514, (1997).

Visentin G.P., et al., "Antibodies from Patients with Heparin-Induced Thrombocytopenia/Thrombosis Are Specific for Platelet Factor 4 Complexed with Heparin or Bound to Endothelial Cells," *J. Clin. Invest.* 93:81-88, (1994).

Warkentin, T.E., et al., "Heparin-Induced Thrombocytopenia: Towards Consensus," *Thrombosis and Haemostasis*, 79:1-7, (1998).

* cited by examiner

DIAGNOSTIC ASSAY FOR TYPE 2 HEPARIN-INDUCED THROMBOCYTOPENIA

RELATED APPLICATIONS

This application is a continuation of International Application No. PCT/US00/23707, which designates the United States and was filed on Aug. 29, 2000, published in English, which claims the benefit of U.S. Provisional Application No. 60/151,314 filed Aug. 30, 1999. The entire teachings of each of these applications are incorporated herein by reference.

GOVERNMENT SUPPORT

The invention was supported, in whole or in part, by grant HL28749 from the National Heart, Lung and Blood Institute of the National Institutes of Health. The Government has certain rights in the invention.

BACKGROUND OF THE INVENTION

Heparin is the injectable anticoagulant of choice for surgical patients requiring either vascular surgery or therapeutic intervention for cardiovascular disease, as well as for the post-surgical management of an immobile (e.g., orthopedic) patient. For example, it is administered to almost all patients during cardiac catheterization, angioplasty, cardiopulmonary bypass and the treatment of unstable angina and myocardial infarction (Bauer, T. L., et al., *Circulation*, 95: 1242–1246 (1997)). However, the therapeutic use of heparin is associated with some serious side effects including the development of heparin-induced thrombocytopenia (Chong, B. H., et al., *Blut*, 58:53–57 (1989)).

Two types of heparin-induced thrombocytopenia with distinct etiologies are recognized. Type 1 is characterized by a relatively mild thrombocytopenia of early onset, that is, within the first few days of heparin therapy. It usually resolves without cessation of heparin (Jackson, M. R., et al., *Surgery* 121:419–424 (1997)). This type of thrombocytopenia is thought to be caused by an intrinsic proaggregatory effect of heparin (Chong, B. H., et al., *Eur. J. Haematol.*, 43:245–251 (1989)). Clinical complications of type 1 thrombocytopenia are uncommon. Type 2 heparin-induced thrombocytopenia (referred to herein as HIT), is a drug-induced, immunoglobulin-mediated thrombocytopenic disorder that is often associated with severe venous or arterial thrombosis attributed to the formation of platelet thrombi (Cines, D. B., et al., *N. Engl J Med*, 31:581 (1987); Celoria, G. M., et al., *Angiology*, 39:915 (1988)). HIT generally occurs 5–8 days following the first exposure to heparin. Platelet counts often drop to less than $100 \times 10^9/l$ and in rare cases to $20 \times 10^9/l$. The incidence of HIT is variable, with rates of occurrences as high as 24–30% reported in some of the earlier studies (Nelson, J. D., et al., *Arch. Intern. Med.*, 138:548–552 (1978); Bell, W. R., et al., *Ann. Intern. Med.*, 85:155–160 (1976)) and with lower values (5–10%) in the more recent studies (Almeida, J. I., et al., *J. Vasc. Surg.*, 27:309–316 (1998); Griffiths, E., and Dzik, W. H., *Trans. Med.*, 7:1–11 (1997); Aster, R. H., *N. Eng. J. Med.*, 332:1374–1376 (1995)). Overall, about 5% of patients receiving heparin develop HIT and about 5–80% of those develop thrombosis, which can involve the arterial, the venous, or both systems (Gupta, A. K., et al., *An. Pharmacol.*, 32:55–59 (1998); Warkentin, T. E., et al., *Am. J. Med.*, 101:502–507 (1996); Chong, B. H., et a., *Br. J. Haematol*, 89:431–439 (1995)). Patients may develop cerebrovascular complications, myocardial infarction, limb ischemia, or deep venous thrombosis. The thrombotic complications are fatal in about 29% of patients, and an additional 21% have limb amputations (King, D. J., et al., *Ann. Intern. Med.*, 100:535–540 (1984)).

It is now widely accepted that immune-mediated (Cancio, L. C., et al, *J. Am. Coll. Surg.*, 186:76–91 (1998); Warkentin, T. E., et al., *Thromb. Haemost.*, 79:1–7 (1998)), and it has been demonstrated that HIT patients produce immunoglobulins reactive with a platelet/heparin complex which, in the presence of pharmacological concentrations of heparin and certain releasable platelet proteins, mediate platelet activation and aggregation, resulting in thrombosis and endothelial cell injury. Because of the underlying immunological mechanism, HIT may occur in patients receiving any preparation of heparin, at any dose, and by any route, including the low heparin concentrations required to maintain the patency of arterial lines (Johnson, R. A., et al., *Am. J. Hematol.*, 17:349–353 (1984)). Any patient who receives heparin is at risk for type 2 heparin-induced thrombocytopenia. No known patient characteristics predict the development of this syndrome. Although an initial sensitization to heparin requires 5–14 days of heparin therapy, thrombosis and thrombocytopenia can occur on the first day of reexposure in a patient previously sensitized to heparin. The time interval required for the manifestation of symptoms can be only hours from the time of heparin reexposure. Consistent with these observations, platelet counts should be obtained before the initiation of heparin therapy and daily thereafter during the course of heparin administration.

The pathophysiology of HIT involves platelet cell surface receptors, and possibly other cell membranes (e.g., endothelial cell membranes bearing platelet factor 4) which bind particular macromolecular heparin/heparin binding protein complexes. For example, it is well established that plasma from HIT patients contains immunoglobulin reactive with a multimolecular complex comprising heparin and platelet factor 4 (PF4). Platelet factor 4 is an abundant tetrameric heparin-binding protein which is stored in platelet α-granules and released by activated platelets. Similarly, thrombospondin-1 (TSP-1) is a 420 kDa glycoprotein present in platelet a granules which accounts for 25% of the total protein secreted by platelets and which contains heparin-binding sequences in its amino terminal globular domain.

HIT-dependent platelet activation is thought to be mediated by the activation of platelet FcγRIIa receptors resulting from the binding of the Fc portion of the IgG component of an antibody/heparin/heparin binding protein complex, which ultimately is deposited onto the platelet surface (Griffiths, E., and Dzik, W. H., *Trans. Med.*, 7: 1–11 (1997); Warkentin, T. E., *Drug Safety*, 17:325–341 (1997)). Furthermore, it has recently been appreciated that HIT IgG is a potent platelet agonist which is able to generate platelet procoagulant activity even more potently than classic platelet agonists (e.g., thrombin and collagen) (Warkentin, T. E., *Drug Safety*, 5:325–341 (1997)). Thus, the procoagulant effects of HIT antibodies and resulting endothelium activation/injury partially explain the high incidence of venous thromboembolism observed in HIT patients.

Early diagnosis of HIT is required to prevent the life-threatening complications that can occur if heparin is continuously administered to a patient producing heparin induced antibodies. It is estimated that the prompt detection of platelet/heparin complex reactive immunoglobulin, and the immediate cessation of heparin administration could reduce the morbidity rate to 7.4–23% and the mortality rate to 1.1–12% (Almeida, J. I., et al., *J. Vasc. Surg.*, 27:309–316 (1998); Laster, J. D., et al., *Surgery*, 102:763–770 (1987)). HIT should be diagnosed on the basis of two criteria: one or more clinical events associated with syndrome (primarily thrombocytopenia), and laboratory evidence for a heparin-dependent immunoglobulin using a sensitive and specific diagnostic assay. Currently, diagnosis of HIT is usually made on a clinical basis and is subsequently confirmed by a positive laboratory test. However, difficulties in diagnosing HIT are common, due primarily to the fact that the laboratory tests which are currently available often produce both false negative and false positive results (Griffiths, E., and Dzik, W. H., *Trans. Med.*, 7:1–11 (1997); Newman, P. M., et al., *Thromb. Haemost.*, 80:292–297 (1998)).

Two standard tests based on platelet aggregation or activation include the platelet aggregation test (PAT) and the $^{14}$C-serotonin release assay (SRA). Currently, the PAT is the most commonly performed laboratory test for diagnosis of HIT. This assay has the advantage of being a non-radioactive test and employs a standard methodology. However, it is considered to be specific but not sensitive, with a false negative rate as high as 50% (Greinacher, A., et al., *Thromb. Haemost.*, 66:734–251 (1991)). The SRA is sensitive and specific and is the recommended assay for HIT (Visentin, G. P., et al., *J. Clin. Invest.*, 93:81–88 (1994); Kelton, J. G., et al., *Blood*, 72: 925–930 (1998); Sheridan, D. C., et al., *Blood*, 67:27–30 (1986)). However this assay employs radiolabeled serotonin and considerable expertise is required to obtain reproducible and reliable results (Kelton, J. G., et al., *Blood*, 72:925–930 (1988); Sheridan, D. C., et al., *Blood*, 67:27–30 (1986)). The reported sensitivity of the PAT has varied from 17% to 81% and that of the SRA from 29% to 94% depending on the study (Cancio, L. C., and Cohen, D. J., *J. Am. Coll. Surg.*, 186:76–91(1998)), a consideration which limits the diagnostic usefulness of both of these standard tests.

Recently, an enzyme-linked immunosorbent assay (ELISA) using a complex of recombinant platelet factor 4 (rPF4) and heparin as a target was developed (Amiral, J. F., et al., *Thromb. Haemost.*, 73:21–28 (1995); Amiral, J. F., et al., *Thromb. Haemost.*, 68:95–96 (1995)). Several recent studies have compared the sensitivity of the rPF4/heparin ELISA with PAT or SRA. Sera from 209 patients were tested in one study (Greinacher, A. J., et al., *Transfusion*, 34:381–385 (1994)) that compared the rPF4/heparin ELISA with the PAT. The ELISA was positive in 33% and the PAT in 11.5% of cases. The improved sensitivity of the rPF4/heparin ELISA has been partly attributed to its ability to detect IgM and IgA antibodies in addition to IgG. The rPF4/heparin ELISA is now commercially available. The rPF4/heparin ELISA uses non-radioactive reagents. However, it produces a high background and is considered to be relatively insensitive (Newman, P. M., et al., *Thromb. Haemost.*, 80:292–297 (1995)).

Published studies evidence the fact that 10 to 50% of test samples evaluated in both a functional assay (e.g., PAT or SRA) and antigen (rPF4 ELISA) assay generate discordant results (Newman, P. M., et al., *Thromb. Haemost.*, 80:292–297 (1998); Greinacher, A. J., et al., *Transfusion*, 34:381–385 (1994); Arepally, G. C., et al., *Am. J. Clin. Path.*, 104:648–654 (1995)). More recently, a multicenter clinical trial of the thrombin inhibitor, argatroban, was conducted in patients with HIT and patients with HIT that had progressed to thrombosis (Walenga, J. M., et al., *Sem. in Hematology*, 36:22–28 (1999)). In this study, three HIT diagnostic assays were investigated: the PAT, the SRA and the ELISA for the antibody to PF4/heparin complex. Confirmation was made in 26%, 55%, and 64% of the patients, respectively (n=199 patients) (Walenga, J. M., et al., *Sem. in Hematology*, 36:22–28 (1999)). Combined results of the three assays enhanced the positive response to 83% of the total population. These data demonstrate that there is no direct correlation between the positive response of these assays, and that clinically positive HIT patients can be missed by all three standard assays.

Thus, there is a need for a sensitive and specific diagnostic assay for the early detection of heparin/heparin binding protein complex-reactive immunoglobulin in the plasma of patients receiving heparin therapy.

SUMMARY OF THE INVENTION

One embodiment of the invention disclosed herein relates to an isolated complex, useful for establishing sensitive and specific immunoassays for the diagnosis of HIT, comprising heparin and the heparin binding proteins platelet factor 4 and thrombospondin-1. More specifically, this embodiment relates to an isolated ternary complex comprising heparin/platelet factor 4/thrombospondin-1 which is formed by the interaction of the components at a ratio determined to be optimal for the formation of a complex which is recognized by heparin-induced immunoglobulin present in a standardized positive control sample. The heparin binding protein components (e.g., platelet factor 4 and thrombospondin-1) can be, for example, intact proteins isolated from human platelets or produced using recombinant means; or biologically active fragments prepared from a protein isolated from human platelets, recombinant proteins, variant recombinant proteins, synthetic peptides and chimeric proteins.

In one embodiment, the invention provides a method for detecting the presence of platelet factor 4/heparin/thrombospondin-1 ternary complex-reactive immunoglobulin in a biological sample. In a second embodiment, the invention provides a method for diagnosing type-2 heparin-induced thrombocytopenia (HIT) wherein the presence of ternary complex-reactive immunoglobulin is indicative of a positive diagnosis of type-2 heparin-induced thrombocytopenia (HIT). An alternative embodiment provides an assay to quantitate the amount of platelet factor 4/heparin/thrombospondin-1 reactive antibody present in a plasma or serum sample wherein a known dilution of a standardized positive control comprising a known amount of ternary complex reactive antibody, and a comparable dilution of a negative control sample are used, and the determination of the amount of ternary complex reactive human antibody present in a test sample comprises measuring the amount of reporter molecule associated with an anti-human immunoglobulin reactive reagent bound to the antibody component of an antigen/antibody complex resulting from the interaction of the samples (e.g., positive control, negative control and test sample) with the platelet factor 4/heparin/thrombospondin-1 ternary complex. A second alternative embodiment of the invention further provides a method for the identification of an individual who is at risk for the occurrence of a thrombotic complication of HIT. More specifically, the identification of this subset of patients relies upon the use of the immunoassay disclosed herein to monitor for the development of ternary complex-reactive immunoglobulin in a plasma or serum sample obtained from a patient during the course of heparin therapy. In a variation of this embodiment the identification of individuals at increased risk of a thrombotic complication can be based on the detection of ternary complex-reactive antibody in a thrombocytopenic patient having a platelet count which is less than about 100,000 to 150,000/mm$^3$.

The invention further relates to kits useful for detecting the presence of immunoglobulin reactive with a platelet factor 4/heparin/thrombospondin-1 antigen complex, comprising one or more reagents for the detection and characterization of platelet factor 4/heparin/thrombospondin-1 ternary complex reactive immunoglobulin. In various embodiments, the kit provides reagents necessary for performing an enzyme linked immunoadsorbent assay (ELISA), a radioimnunoassay, an immunofluorescence assay and a flow cytometry assay. One embodiment of this aspect of the invention is an ELISA kit useful for diagnosing HIT, comprising reagents necessary to produce a platelet factor 4/heparin/thrombospondin-1 ternary complex, and suitable reagents for the detection, characterization and quantification of ternary complex reactive immunoglobulin present in test samples. Alternative kit embodiments may optionally comprise a solid phase support suitable for the immobilization of the ternary complex and/or positive and negative control samples derived from a pool of HIT patient plasma or healthy human donors who have never received heparin, respectively, for the standardization of the assay. An alternative kit embodiment of the invention may comprise a solid phase support material supplied precoated with a platelet factor 4/heparin/thrombospondin-1 ternary complex.

BRIEF DESCRIPTION OF THE DRAWINGS

FIG. 5A illustrates the effects of varying the heparin concentration (0–1 U/ml) admixed with a constant amount of TSP-1 (20 µg/ml) on the binding of HIT patient antibodies.

FIG. 5B illustrates the effects of varying the TSP-1 concentration (1.25–40 µg/ml) admixed with a constant amount of heparin (0.03 U/ml) on the binding of HIT patient antibodies.

FIG. 5C illustrates the effects of varying the TSP-1 concentration (0.1–5 µg/ml) admixed with a constant amount of heparin (0.03 U/ml) on the binding of HIT patient antibodies. Results are expressed as the mean±SEM.

FIG. 7 presents two graphs comparing ELISA results obtained using a commercially available ELISA kit and the PF4/heparin/TSP-1 method disclosed herein to detect the presence of heparin/heparin binding protein complex reactive antibodies in the sera of 36 known HIT patients and 10 healthy subjects.

DETAILED DESCRIPTION OF THE INVENTION

Figure 1A:
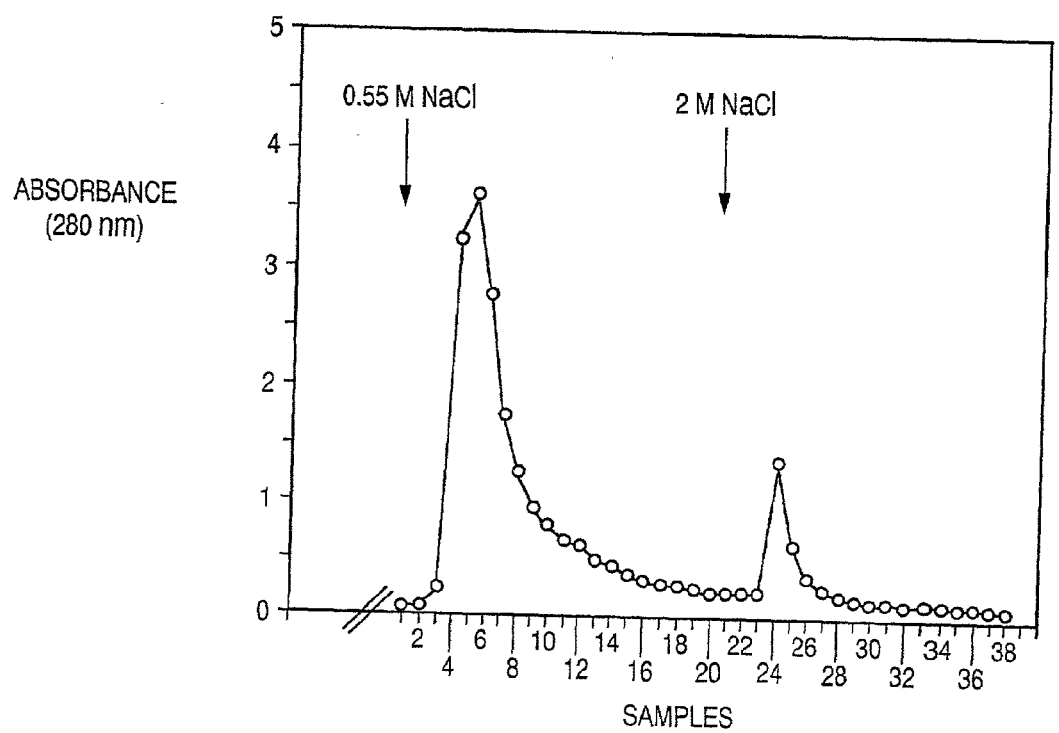
FIG. 1A represents the elution profile of thrombospondin-1 (TSP-1) and platelet factor 4 (PF4) from a heparin-Sepharose 6B column.
Figure 1B:
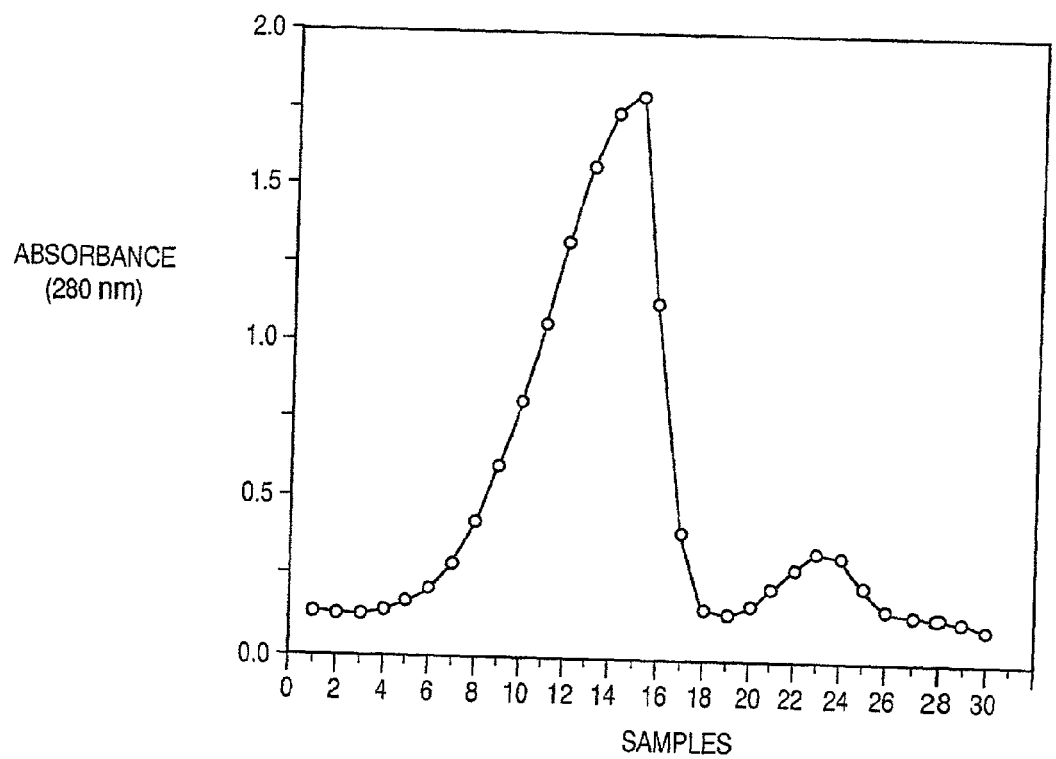
FIG. 1B illustrates the distribution of TSP-1 in a sucrose density gradient (10–20%). The first peak corresponds to TSP-1 and the last peak corresponds to low molecular weight proteins including β-thromboglobulin.

Described herein is an isolated ternary complex comprising heparin/platelet factor 4/thrombospondin-1 useful for establishing sensitive and specific immunoassays for the detection of heparin-induced ternary complex-reactive immunoglobulin (e.g., antibody) in the plasma or serum of patients receiving heparin therapy. The presence of this immunoglobulin and its specificity for a platelet/heparin complex is indicative of type 2 heparin-induced thrombocytopenia, a diagnosis which identifies patients at increased risk for a thrombotic complication, and provides clinicians with an opportunity to reduce HIT-mediated morbidity and mortality. The invention also relates to methods of detecting the presence of platelet factor 4/heparin/thrombospondin-1 ternary complex reactive immunoglobulin in a biological sample (e.g., plasma or serum sample) obtained from a patient receiving heparin therapy.

The presence of ternary complex reactive immunoglobulin can be detected in biological samples, for example, plasma or serum samples obtained from patients receiving any preparation of heparin, at any dose, and by any route (e.g., intravenous, intramuscular, subcutaneous or a combination thereof), including the low heparin concentrations required to maintain the patency of arterial lines. For example, suitable plasma samples can be obtained from patients receiving heparin therapy in the case of, for instance, vascular surgery, cardiac catheterization, angioplasty, cardiopulmonary bypass, treatment of unstable angina, treatment of myocardial infarction or the post-surgical management of thrombotic risk in an immobile (e.g., orthopedic) patient.

The methods described herein can be easily adapted to assess the presence of antibodies reactive with any form of heparin drug including but not limited to: porcine intestinal mucosal heparin (e.g., unfractionated or low molecular weight heparin (LMWH)), bovine lung heparin, metal heparinates, heparinoids, and heparin fragments. The terms "heparin" and "heparin drug" are used synonymously herein. Heparin (e.g., heparin drug) is a highly sulfated member of the family of glycosaminoglycans whose other members include heparin sulfate, chondroitin sulfate, dermatan sulfate and keratan sulfate. Unfractionated heparin is a heterogenous mixture of glycosaminoglycans, which is produced commercially from pork intestinal mucosa or beef lung. As in other glycosaminoglycans, two monosaccharides alternate to form a polymer; one of the monosaccharides is an aminohexose (i.e., contains an amino group at carbon 2), and the other is an acid monosaccharide (i.e., contains a carboxyl group at carbon 5). In the case of heparin, these monosaccharides are derived from glucosamine and uronic acid and contain multiple additional sulfate groups. The molecular weight of heparin varies from molecule to molecule and ranges from 3,000 to 30,000 daltons (mean, 15,000). Under physiologic conditions, heparin's multiple sulfate and carboxyl groups are dissociated and render it a polyanion.

As used herein the term "low molecular weight heparins" (LMWH) refers to heparin derived from unfractionated heparin by chemical or enzymatic depolymerization and fractionation, which have a mean MW of 4,000 to 6,500, depending on the process used. As used herein the term "heparinoid" encompasses a mixture of anticoagulant glycosaminoglycans (Meuleman, D. G., *Haemostasis*, 22:58–65 (1992)). For example, a heparinoid can be isolated from porcine intestinal mucosa. The heparinoid danaparoid sodium (Org 10172) consists of 84% heparin sulfate (approximately 5% with high antithrombin affinity), 12% dermatan sulfate, and 4% chondroitin sulfate. Danaparoid sodium can be used to treat HIT because: (i) it produces less non-idiosyncratic platelet activation than both unfractionated heparin and LMWH (Makhoul, et al., *J. Vasc. Surg.*, 4:522–528 (1986); Mikhailidis, D. P., et al., *Br. J. Clin. Pharmacol.*, 17:43–48 (1984), (ii) it is associated with a lower frequency of cross-reactivity for HIT antibodies than both unfractionated heparin and LMWH (Vun, C. M., et al., *Thromb. Res.*, 81:525–532 (1996); Greinacher, A., et al., *Thromb. Haemost.*, 67:545–549; Chong, B. H., et al., *Blood*, 73:1592–1596 (1995) and (iii) HIT-like illness has not been reported in patients who have received only danaparoid sodium for prophylaxis or treatment of thrombosis (Warkentin, T. E., *Drug Safety*, 17:325–341 (1997)). One potential disadvantage of danaparoid sodium to treat HIT is the risk of in vitro and in vivo cross-reactivity of this agent for HIT-antibodies (Warkentin, T. E., Drug Safety, 17: 325–341 (1997)). However, danaparoid sodium has a much lower risk of in vitro cross-reactivity (approximately 10 to 20%) than LMWH preparations (>90%) (Vun, C. M., et al., *Thromb. Res.*, 81:525–532 (1996); Greinacher, A., et al., *Thromb. Haemost.*, 67:545–549 (1992); Chong, B. H., et al., *Blood*, 73:1592–1596 (1995)). Like LMWH, Org 10172 has an average molecular weight (6000) that is less than that of unfractionated heparin. It is not a heparin byproduct; rather, it is prepared directly from intestinal mucosa by a different process and contains heparin sulfate, dermatan sulfate, and chondroitin sulfate (Meuleman, D. G., *Haemostatis*, 22(2): 58–65 (1992)).

As used herein the term "heparin-like compound" can include any member of the family of glucosaminoglycans whose other members include heparan sulfate, chondroitin sulphate, dermatan sulfate and keratan sulfate. It is now widely accepted that LMWH as well as other sulfated polysaccharides can bind to HIT antibodies in the presence of PF4, and their reactivity is dependent on the molecular weight and the sulfation grade (Amiral, et al., *Thromb. Haemost.*, 73:21–28 (1995); Chong, B. H., *Br. J. Haematol.*, 89:431–439 (1995)).

As used herein, the term "isolated" is intended to mean that the material in question exists in a physical milieu distinct from that in which it occurs in nature and/or that the material has been completely or partially purified from other materials present in the starting material. For example, an "isolated protein" suitable for use in the disclosed immunoassay, as a component of an antigenic complex useful for assessing the presence of platelet/heparin reactive immunoglobulin, may be substantially purified protein (e.g., a protein which migrates as a single band upon SDS-PAGE) with respect to the complex cellular milieu in which it naturally occurs. In some instances, the isolated material could comprise part of a composition (e.g., a crude cellular extract containing other substances), buffer system or reagent mix. In other instances, the material may be purified essentially to homogeneity, for example, as determined by column chromatography (e.g., HPLC) or polyacrylamide gel electrophoresis (PAGE), but may also have exogenous cofactors or molecular stabilizers added to the purified protein product. In one embodiment, proteins or polypeptides are isolated to a state of at least about 75% pure; more preferably at least about 85% pure, and still more preferably at least about 95%, as determined by Coomassie blue staining of proteins on SDS-polyacrylamide gels, or Western Blot analysis.

Suitable heparin binding proteins (e.g., PF4 or TSP-1) or polypeptides for use in the present invention can be purified from a natural source (e.g., from mammalian blood, for example from human platelets), isolated from a purified protein, synthesized based on the amino acid sequence of the human protein, made recombinantly, or purchased from a commercial source. Heparin binding proteins can be purified from human platelets, or from recombinant host cells, according to the methods provided herein, or alternatively they can be purified according to techniques such as heparin-Sepharose chromatography, gel filtration chromatography, ammonium sulfate precipitation and/or sucrose gradient ultracentrifugation. Additional known methods useful for protein or polypeptide purification include ethanol precipitation, acid extraction, anion or cation exchange chromatography, hydrophobic interaction chromatography, affinity chromatography and high performance liquid chromatography. Known methods for refolding protein can be used to regenerate active conformation if the polypeptide is denatured during isolation or purification.

With respect to proteins purified from a natural source, the term "isolated protein" describes any protein which has been purified to a state beyond that in which it exists in the cell in which its biosynthesis occurs, and includes proteins obtained by the methods described herein, similar methods known to those of skill in the art, or other equivalent methods. The term "isolated protein" also contemplates proteins or polypeptides produced by chemical synthesis or by a combination of biological and chemical methods, and encompasses, but is not limited to, isolated recombinant proteins chimeric proteins and fusion proteins. Chimeric or fusion proteins can be produced by numerous methods which are well known to one of skill in the art.

In the platelet factor 4/heparin/thrombospondin-1 ternary complex: i) heparin can be substituted by LMWH, any glycosaminoglycan (heparin sulfate, chondroitin sulfate, dermatan sulfate and keratan sulfate) and any heparinoid or any heparin-like compound, ii) platelet factor 4 can be substituted by a purified recombinant platelet factor 4 or recombinant variant platelet factor 4 (such as a chimeric variant), or one or more biologically active fragments thereof, iii) thrombospondin-1 can be substituted by a purified recombinant thrombospondin-1 or recombinant variant thrombospondin-1 (such as a chimeric variant or fusion protein of thrombospondin-1), or one or more biologically active fragments thereof. As used herein, the term "biologically active fragment" encompasses fragments (e.g., portions and peptides) of a ternary complex component (platelet factor 4/heparin/thrombospondin-1) which contain binding sites for interaction with the other components of the ternary complex and epitopes for recognition by HIT antibodies which recognize the ternary complex. They are capable of functioning like the full-length component in the sense that they interact with complex specific antibodies when they are present in a ternary complex.

TSP-1, a 420,000 dalton adhesive glycoprotein, is composed of three subunits of equivalent molecular weight (Lawler, J., et al., *J. Biol, Chem.,* 260:3762–3772 (1985)). Structurally, TSP-1 displays two types of organization. At the $NH_2$- and the COOH-terminals there are regions that do not have strong sequence similarity to other proteins, do not have multiple copies of amino acid sequence motifs, have few cysteine residues, and appear as globular domain by electron microscopy (Lawler, J., et al., *J. Biol, Chem.,* 260:3762–3772 (1985)). The $NH_2$-terminal globular domain has been shown to contain a heparin-binding site (Lawler, J., and Slayter, H. S., *Throm. Res.,* 22:267–279 (1981); Dixit, V. M., et al, *J. Biol. Chem.,* 259:10100–10105 (1984)). The high-affinity heparin-binding site has been shown to be included in the first 218 amino acids of the mature TSP-1 peptide (Prochownik, E. V., et al, *J. Biol. Chem.,* 109: 843–852 (1989)). There are two sequences within the $NH_2$-terminal of TSP-1 that conform to the consensus sequences for heparin-binding sites. These are RKGSGRR (SEQ. ID NO: 1) and RQMKKTR (SEQ ID NO: 2). The center portion of each TSP-1 monomer comprises regions that are homologous to other proteins, are composed of multiple copies of amino acids sequence motifs, are rich in cysteine residues and appear thin and extended by electron microscopy (Lawler, J., and Hynes, R. O, *J. Cell Biol,* 103:1635–1648 (1986)). The WSXW (SEQ ID NO: 3) sequence present in type 1 repeats also appears to function as a novel type of heparin-binding domain. Consistent with these observations, Dardick and Lahav (*Eur. J. Biochem.,* 168:347–355 (1987)) mapped a low-affinity heparin-binding site to a 70,000-dalton polypeptide that comprises the central portion of each subunit. The interchain disulfides, the region of homology with procollagen, and type 1 and type 2 repeats are included within the 70,000-dalton region. Furthermore, Lawler, J., et al., (*Biochemistry,* 31:1173–1180 (1992)) showed that polypeptides that lack the type 1 or type 2 repeats retain the low-affinity heparin binding site. These data suggest that heparin-binding sites are present in both the middle portion and the COOH terminus of the TSP-1 monomer.

Because multiple TSP-1 domains can interact with heparin and are involved in its interaction with various classes of cell surface receptors (Frazier, W. A., *Curr. Opin Cell. Biol.,* 3:792–799 (1991); Adams, J. C., and Lawler, J, *J. Cell. Sci.,* 104:1061–1071 (1993); Bornstein, P., and Sage, E. H., *Methods Enzymol.,* 245:62–85 (1994)), multiple regions of the TSP-1 molecule (e.g., $NH_2$- and COOH-terminals, procollagen domain, type 1 repeat, type 2 repeat, type 3 repeat) are likely: (1) to be involved in PF4/heparin/TSP-1 ternary complex formation; (2) to be recognized by HIT antibodies; and (3) to mediate its interaction with platelet TSP-1 receptors (e.g., CD36, CD47, $\alpha v \beta 3$). PF4, a 70-amino acid platelet specific protein, belongs to the CXC chemokine subfamily, in which the first two of the four conserved cysteine residues are separated by one amino acid residue (Rollins, J. R., *Blood,* 90:909 (1997)). PF4 has been sequenced (Deuel, et al., *Proc. Natl. Acad. Sci. USA,* 78:4854–4887 (1981)) and cloned (Ponz, M., et al., *Blood,* 69:219–223 (1987)), and its x-ray crystallographic structure has been defined (St. Charles, et al., *J. Biol. Chem.,* 264: 2092–2099 (1989); Zhang, X., et al., Biochemistry, 33:8361–8366 (1994)). PF4 exists as a tetramer with the three beta sheets of each subunit facing inwards and the N- and the C-termini lying on the surface of the molecule. The C-termini are rich in lysines, which contribute to the tetramer's high affinity for heparin. The mechanism by which PF4/heparin complexes become antigenic and the portion(s) of PF4 that we recognized by HIT antibodies remain unknown.

In one embodiment, the invention provides a method for the detection of platelet factor 4/heparin/thrombospondin-1 ternary complex reactive immunoglobulin in a biological sample, the method comprising: contacting a test biological sample (e.g., serum or plasma) with a solid phase-immobilized ternary complex (platelet factor 4/heparin/thrombospondin-1) thereby producing a first combination; maintaining the first combination under conditions suitable to promote the formation of antigen/antibody complexes, referred to as a first product; contacting the resulting product with a detectably-labeled anti-human immunoglobulin reactive reagent specific for at least one isotype of human immunoglobulin, thereby producing a second combination; maintaining the second combination under conditions suitable to promote the binding of the anti-human immunoglobulin reagent to the antibody component of the above-defined first product; and detecting the presence of said detectable label (reporter molecule), wherein the detection of the label demonstrates the presence of immunoglobulin reactive with the ternary antigen complex. In a second embodiment, the invention provides a method for the diagnosis of HIT comprising detecting the presence of ternary complex reactive immunoglobulin in a biological sample obtained from a patient receiving a heparin drug, wherein the presence of complex-reactive immunoglobulin is indicative of type 2 heparin-induced thrombocytopenia.

Suitable solid phase support materials for use in the immunoassay embodiment of the instant invention include, but are not limited to materials selected from the group consisting of polycarbonate, polyallomer, polypropylene, polyvinyl, nylon, nitrocellulose, polystyrene and maleic anhydride activated polystyrene. Heparin/heparin binding protein complexes are preformed (e.g., prior to immobilization on the solid phase support material) at a ratio which is empirically determined to produce a ternary complex that is capable of being recognized by the heparin-induced immunoglobulin that is anticipated as being characteristic of the patient sample being analyzed. For example, for a patient receiving unfractionated porcine intestinal mucosal heparin, then this form of heparin or a derivative (e.g., a fragment, peptide or chimeric protein derived from porcine intestinal mucosal heparin) of this form can be used to formulate the heparin/heparin binding protein complex. Similarly, for a patient treated with bovine lung heparin, then bovine lung heparin, or a derivative, can be incorporated into the antigenic complex utilized to assess the presence of heparin-induced immunoglobulin.

The optimal ratio of complex components can be determined according to the method described herein, or according to other equivalent methods well known to those of skill in the art. Optimization of the PF4/heparin/TSP-1 ELISA discussed herein is dependent upon the ratio at which the PF4, heparin and TSP-1 molecules are combined and the structure of the resulting ternary complex. The coating solution used for binding antibodies generated in type 2 HIT patients, was a mixture of unfractionated heparin and human PF4 and TSP-1 protein purified from platelets. As reported herein, optimization was accomplished by mixing variable amounts of PF4 and TSP-1 with different concentrations of unfractionated heparin in a binding buffer (e.g., 0.05 M phosphate buffer, 0.15 M NaCl at pH 7.2), thereby creating a coating solution appropriate for use in preparing a solid phase surface (e.g., microtiter assayplate wells) for use in the methods described herein. Using these particular components, the optimal ratio for forming a ternary complex recognized by HIT patient's plasmas is 20 $\mu$g/ml PF4, 0.03 U/ml unfractionated herparin and 1 $\mu$g/ml TSP-1.

Depending on the (i) nature of the proteins used (proteins isolated from human platelets, fragments prepared from a protein isolated from human platelets, recombinant human proteins, synthetic peptide, recombinant human protein or chimeric human protein), (ii) the form of heparin (unfractionated heparin, LMWH, heparinoid or any form of glycosaminoglycan including heparin, heparin sulfate, chondroitin sulphate, dermatan sulfate and keratan sulfate) used, and (iii) the nature of the solid phase material used (polycarbonate, polyallomer, polypropylene, polyvinyl, nylon, nitrocellulose, polystyrene or maleic anhydride activated polystyrene), appropriaate ratios for the formation of a ternary complex suitable for use in the methods disclosed herein can comprise 0.01–40 $\mu$g/ml PF4, 0.01–1 U/ml unfractionated heparin and 0.01–40 $\mu$g/ml TSP-1. For example, as shown herein, a suitable ratio at which to combine the component proteins is 20 $\mu$g/ml human PF4 (purified from platelets), 0.03 U/ml unfractionated heparin and 1 $\mu$g/ml human TSP-1 (purified from platelets). Other embodiments of the invention include ternary complexes produced by combining a heparin drug, PF4 and TSP-1, wherein the PF4:TSP-1 ratio (as expressed in weight/volume of each protein) is between about 1:200 and about 200; between about 1:100 and about 100; between about 2:100 and about 50; and between about 4:100 and about 25. Further embodiments of the invention include methods for detecting the presence of immunoglobulin in a biological sample wherein heparin is combined with PF4 and TSP-1, wherein the PF4 and TSP-1 are combined using the above ratios. A skilled artisan will recognize that the optimal ratio will vary depending upon the nature of the proteins used, the form of heparin and the nature of the solid phase material, and will therefore expect to perform some routine experiments to optimize different embodiments of the methods described herein.

The ternary complex can subsequently be immobilized onto a suitable solid phase support material. For example, the preformed complex can be immobilized onto the wells of a polystryene microtiter plate by contacting the wells with the coating solution (e.g., 0.05 M phosphate buffer, 0.15 M NaCl at pH 7.2) comprising the preformed complex. For example, the solution can be contacted with the microtiter plate for approximately 12 hours (e.g., overnight) at a temperature of 4° C. Unoccupied binding sites can be subsequently blocked, to prevent the nonspecific adherence of the human immunoglobulin reactive reagent, by adding 10% (vol/vol) species matched (relative to the species of the anti-human immunoglobulin reagent) serum in phosphate-buffered saline (PBS) for at least about 2 hours, at a temperature of from about 4° C. to about room temperature. Excess blocking solution can subsequently be removed by washing with an excess volume of wash buffer (e.g., PBS Tween) at least about three times. Test samples (e.g., patient plasma or serum) to be assessed can be obtained from patients receiving a heparin drug, and who are therefore suspected of producing heparin-induced immunoglobulin, and prepared for use in the immunoassay described herein by diluting the plasma into an assay buffer which is most often formulated to be identical to the blocking buffer exemplified above. In general, a suitable dilution buffer is formulated to minimize the background binding of the anti-human immunoglobulin reactive reagent selected for use. For example, if the anti-human immunoglobulin reagent selected for the detection of the complex-reactive immunoglobulin is a polyclonal goat anti-human reagent, then an appropriate assay buffer can comprise from about 5 to 10% normal goat serum in PBS. The diluted test sample is contacted with the immobilized heparin/heparin binding protein complex and maintained under conditions suitable to promote the formation of antigen/antibody complexes referred to as a first product. For example, suitable conditions to promote the formation of antigen/antibody complexes comprise, but are not limited to, a length of time of between approximately 60 minutes and approximately 120 minutes at a temperature of from between about 25° C. to about 37° C. The presence of heparin-induced immunoglobulin can be determined by creating a second combination comprising the washed antigen/antibody complex resulting from the first combination with an anti-human immunoglobulin reactive reagent specific for at least one isotype of human immunoglobulin having a reporter molecule conjugated to it, and maintaining the second combination under conditions suitable to promote the binding of the anti-human immunoglobulin specific reagent to the antibody component of said first product.

Depending upon the nature of the heparin therapy which the patient was receiving and the clinical profile of the patient at the time when the plasma sample is obtained, an investigator may choose to assess the level of either human IgM, IgG or IgA. In the alternative, an investigator may choose to use a polyclonal reagent specific for all isotypes of human immunoglobulin, thereby using the assay to merely detect the presence of ternary complex reactive immunoglobulin without determining isotype specific titers. Suitable polyclonal reagents can be produced in any immunocompetent animal capable of mounting a humoral immune response to exogenously administered human immunoglobulin. Typically, appropriate anti-human immunoglobulin reactive reagents are produced in goats, or rabbits, and occasionally donkeys.

As used herein, the term "anti-human immunoglobulin reactive reagent" is intended to encompass not only polyclonal antibody preparations comprising intact host species immunoglobulin, but also any form, portion or fragment of an antibody molecule capable of interacting with human immunoglobulin, including for example F(ab)2 and F(ab) fragments of immunoglobulin and chimeric antibodies. The term also encompasses monoclonal antibody preparations which are specific for human immunoglobulin.

Applicants have exemplified assay conditions suitable to promote the binding of the anti-human immunoglobulin reagent as incubation for a length of time between approximately 30 minutes and approximately 60 minutes at a temperature from between about 25° C. to about 37° C. As used herein the term "detectably-labeled anti-immunoglobulin reactive reagent" encompasses reagents comprising a label (reporter molecule) selected from, but not limited to, an enzyme, a radioactive molecule, an affinity ligand and fluorophore. The presence of heparin-induced immunoglobulin is subsequently determined by detecting and quantifying the label (reporter molecule) using a method that is dependent on the nature of the label, for example, by adding the substrate for a particular enzyme, or determining the fluorescence of a fluorophore conjugated anti-human immunoglobulin. Appropriate enzyme labels for use in the instant invention include, but are not limited to, horseradish peroxidase, alkaline phosphatase, β-galactosidase and glucose oxidase. Biotin represents an appropriate affinity ligand for use in the disclosed invention, which, when used with streptavidin by methods known in the art, provides a means for separation and isolation of a biotin-tagged assay component, for example, a means of amplifying the specific detection of anti-immunoglobulin reagent. Appropriate substrates for the above listed enzyme labels include, but are not limited to: Tetramethyl Benzidine (TMB), O-Phenylenediamine Dihydrochloride (OPD), 2,2'-Azinobis (3-ethylbenzothiazoline-6-sulfonic acid-Diammonium salt (ABTS), for horseradish peroxidase; p-Nitrophenyl Phosphate, Disodium salt (PNPP), for alkaline phosphatase; O-Nitrophenyl-b-D-Galactopyranosidase (ONPG), Naphthol-AS-BI-β-D-Galactopyranosidase (Nap-Gal), 4-methyl-Umbelliferyl-β-D-Galactopyranoside (Mum-Gal), for β-Galactosidase; and Phenazine Methosulfate (PMS) for glucose oxidase. Appropriate fluorochromes include, but are not limited to fluorescein, phycoerythrin and rhodamine.

The incorporation of standardized controls into the immunoassay described herein renders the assay quantitative. For example, to quantitate the ternary complex-reactive human immunoglobulin present in an unknown test sample, the assay can be standardized by using a known dilution of a positive control comprising a known amount of ternary complex reactive immunoglobulin (obtained from HIT complex positive HIT patients) and an equivalent dilution of a negative control (e.g., obtained from a healthy normal donor). In practice, the standardized assay will include a step of measuring the amount of reporter molecule associated with the labeled anti-human immunoglobulin reactive reagent bound to ternary complex-reactive immunoglobulin by means of a reaction that can be evaluated relative to a comparable reaction of the standardized positive control. A positive result can be defined as one that was greater than the mean of the value of the absorbance for healthy subjects plus 3 standard deviations and values below that were considered negatives.

It is to be understood that skilled artisans will know that the exemplified time periods, assay temperatures, and suggested reporter molecules, buffers and/or diluents have many equivalents which can easily be identified and interchanged with the suggestions and examples provided herein.

An alternative embodiment the invention provides a diagnostic assay for the identification of individuals at increased risk for the occurrence of a thrombotic complication of HIT. More specifically, this embodiment of the invention comprises the steps of: contacting a plasma or serum sample obtained from a patient receiving heparin therapy with the immobilized heparin/heparin binding protein complex, thereby forming a first combination; maintaining the first combination under appropriate conditions to promote the formation of an antibody/antigen complex, wherein the antibody is derived from the plasma sample and the platelet factor 4/heparin/thrombospondin-1 ternary complex is the antigen; and detecting the presence of the antibody/antigen complex. The detection of ternary complex-bound immunoglobulin in a sample obtained from a patient receiving heparin therapy is indicative of an increased risk of a thrombotic complication and is diagnostic for type-2 heparin induced thrombocytopenia. In the majority of HIT cases the antibody mediating a thrombotic complication is IgG. However, in about 30% of HIT patients thrombocytopenia and thrombotic complications can be induced by IgM and/or IgA in the absence of IgG. Thus, the diagnostic assay disclosed herein can be used to confirm a clinical diagnosis of HIT and identify individuals at increased risk for thrombotic complication by basing a diagnosis on the combined presence of ternary complex-reactive immunoglobulin and a determination that the individual's platelet count is less than about 100,000–150,000/mm$^3$.

The invention further includes kits for diagnosing HIT, comprising one or more reagents for detecting the presence of platelet factor 4/heparin/thrombospondin-1 ternary complex reactive immunoglobulin. In various embodiments, a kit may provide reagents necessary for performing an enzyme linked immunoadsorbent (ELISA), a radioimmunoassay, an immunofluorescence assay or a flow cytometry assay. One embodiment of this aspect of the invention comprises an enzyme linked immunoadsorbent assay (ELISA) kit useful for diagnosing HIT comprising, in separate containers: a buffered medium comprising a heparin, a buffered medium comprising isolated human platelet factor 4; a buffered medium comprising isolated human thrombospondin-1; a wash medium formulated to reduce nonspecific binding; at least one immunoreactive reagent having a reporter molecule conjugated thereto and a specificity for at least one isotype of human immunoglobulin; a substrate for the reporter molecule; a standardized positive control comprising a known amount of ternary complex antibody; a negative control sample and a diluent reagent.

Alternative kit embodiments may further comprise a solid phase support suitable for the immobilization of a platelet factor 4/heparin/thrombospondin-1 ternary complex, or a solid phase support material that is precoated with a platelet factor 4/heparin/thrombospondin-1 ternary complex.

Figure 8:
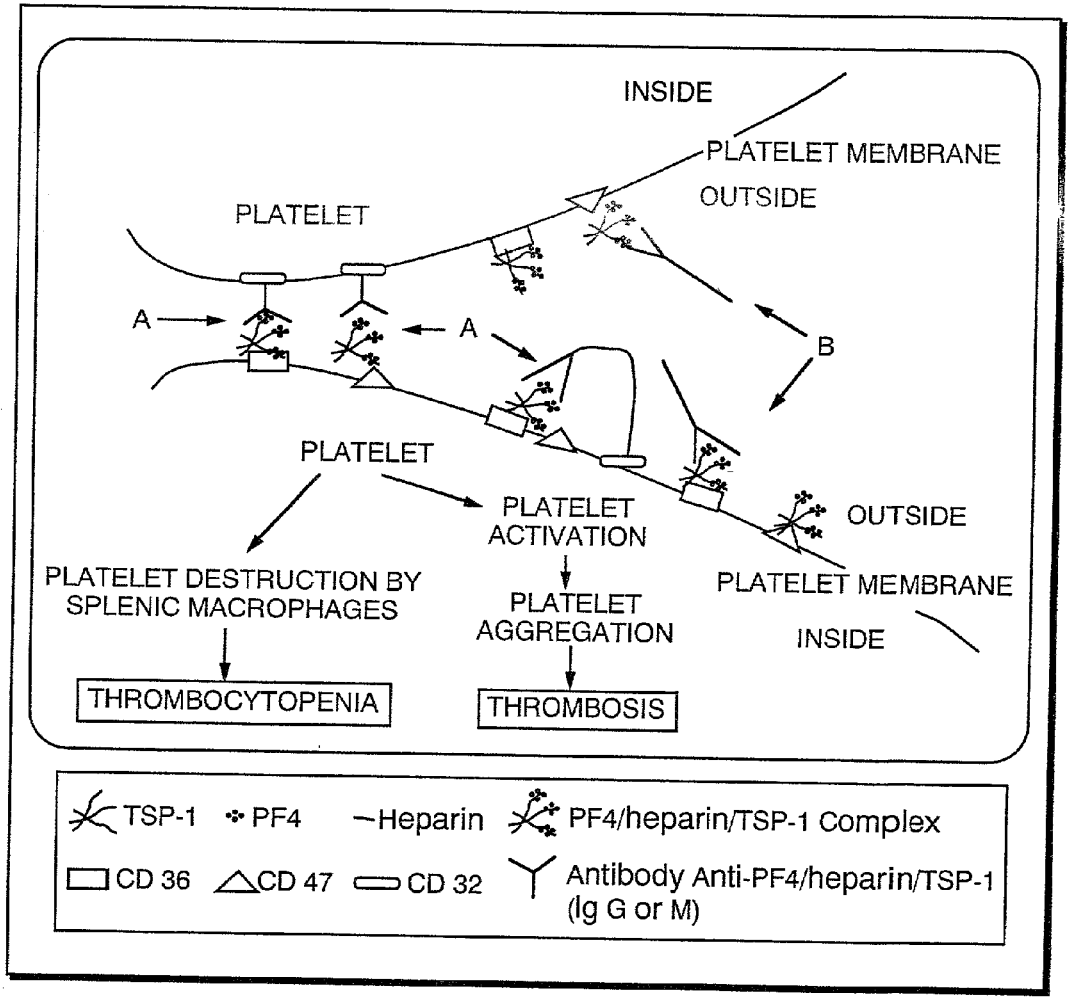
FIG. 8 is a schematic illustration summarizing a proposed new model for the pathogenesis of type 2 heparin-induced thrombocytopenia and thrombotic injury. Briefly, the binding of PF4/heparin/TSP-1 complexes to platelets via CD36 and/or CD47 is predicted to promote the generation of anti-PF4/heparin/TSP-1 antibodies. Resulting multimolecular complexes of PF4/heparin/TSP-1 and antibodies formed on the platelet membrane subsequently mediate the cross-linking of CD32 and/or CD36 and CD47 (A: if the antibodies are of the IgG class), or CD36 and/or CD47 (B: if the antibodies are the IgA and IgM class). Binding of the immune complexes to platelet leads to (i) platelet activation, aggregation and thrombosis and (ii) also to platelet removal by the spleen and thrombocytopenia. Other TSP-1 platelet receptors are not presented to simplify the Figure.

While not wishing to be bound by any specific mechanism, Applicants propose the following model for the pathogenesis of HIT and thrombosis as consistent with experimental results described herein (See FIG. 8).

In the α-granules, PF4 is bound to a proteoglycan carrier that contains chondroitin-4-sulfate (Fukami, M. H., et al., Thromb. Res., 14:433–443 (1979); Barber, A. J., et al., Biochim. Biophys. Acta., 286:312–329 (1972)). Since PF4 binds to glycosaminoglycans roughly in order of their negative charge density (Handin, R. I., and Cohen, H. J., J. Biol. Chem., 251: 4273–4282 (1976)), the tetramer is predicted to easily transfer to more sulfated polysaccharides such as heparin when the carrier complex is released from the platelets (Stuckey, J. A., et al., Proteins, 14:277–287 (1992)). Because both PF4 and TSP-1 bind heparin, it is likely that TSP-1 and PF4, in the presence of physiologic concentrations of heparin, bind to each other, thereby resulting in the formation of PF4/heparin/TSP-1 complexes. TSP-1 is known to bind to the platelet surface via a number of receptors, which include but are not limited to sulfatides (which bind to the $NH_2$-terminal heparin binding domain), GP IV or CD36 (which binds to a region within the type 1 repeats) and $\alpha v\beta 3$ and $\alpha IIb\beta 3$ (both of which have been shown to bind TSP-1 in an RGD-dependent manner) (Lawler, J., Blood, 67:1197–1209 (1986); Lawler, J., J. Cell. Biol., 107:2351–2361 (1986)). Gao, et al., have recently reported that the integrin-associated protein (IAP or CD47) is a receptor for the COOH-terminal domain of TSP-1 (Gao, A. G., et al., J Biol. Chem., 271:21–24 (1996)). Applicants suggest that the binding of PF4/heparin/TSP-1 complexes to platelets via CD36, $\alpha v\beta 3$ and/or CD47 leads to the generation of anti-PF4/heparin/TSP-1 antibodies. Multimolecular complexes of PF4/heparin/TSP-1 and antibodies formed on the platelet membrane may lead to cross-linking of CD32 and/or CD36, $\alpha v\beta 3$ and CD47. This interaction is predicted to mediate potent platelet activation and aggregation.

EXAMPLES

Materials and Methods

Test Samples: Plasma samples from 36 patients who developed thrombocytopenia (platelet count<1000,000/$mm^3$, or a decrease of 30–40% from baseline value) while receiving heparin, and who were referred to the Hematology Laboratory at Hotel-Dieu Hospital in Paris for the detection of heparin-dependent antiplatelet antibodies, were kindly provided by Dr. Ismail Elalamy. All the patients had a progressive platelet drop, occurring after at least 5 days of heparin therapy. In addition, ten plasma samples obtained from healthy subjects were obtained from the blood bank at Hotel-Dieu Hospital in Paris, for use as normal (e.g., negative) controls. Standard Platelet Aggregation Test: A standard platelet aggregation test was performed as described previously (Chong, B. H., et al., Thromb. Haemost., 69:344 (1993)). Briefly, platelet rich plasma is admixed with duplicate test plasma samples and maintained at 37° C. in an aggregometer. Sufficient heparin is added to one aliquot of each paired sample to produce a low- and high-concentration of 0.5 U/ml and 100 U/ml (final concentration), respectively. The degree of aggregation is assessed by determining the increase in light transmittance. Plasmas are considered positive if there is more than 20% platelet aggregation at the low, but not the high, heparin concentration.

Reagents: Polyclonal rabbit anti-human PF4 antibody (Propr. Tech INC, Rocky Hill, USA) and monoclonal murine anti-human TSP-1, MA I, (Lawler, J., et al., Biol. Chem., 260:3762–3772 (1985)) were used to identify the purity of isolated PF4 and TSP-1 by immunoblotting.

Unfractionated heparin (specific activity, 177 U/mg) was obtained from Celsus Laboratories (Cincinnati, Ohio, USA). Recombinant platelet factor 4 was obtained from American Research Products Inc., (Belmont, Mass., USA).

The following products were obtained from Pierce (Rockford, Ill., USA): Reacti-Bind™ maleic anhydride activated polystyrene plates, untreated polystyrene plates, goat serum, orthophenylene diamine (OPD) substrate, peroxidase conjugated goat antihuman IgG, IgA, IgM and Tween-20.

Enhanced chemiluminescence (ECL) reagent was from Amersham Pharmacia Biotech., (Piscataway, USA). XAR films were obtained from Eastman Kodak Co., (Rochester, N.Y., USA). Centriplus Concentrators was obtained from Amicon Inc., (Beverly, Mass., USA).

Protein concentrations were determined using Bio-Rad Dc Protein assay (Hercules, USA) with bovine serum albumin as a standard, according to manufacturer's instructions.

Asserachrom rPF4/heparin ELISA Kit was purchased from Stago Diagnostica (France).

Statistical Analysis.

ELISA Data are presented as mean±SEM. The statistical significance was analyzed by Student's t-test for paired data. Values were considered statistically significant when $P<0.05$.

Example 1

Isolation of PF4 and TSP-1.

Figure 2:
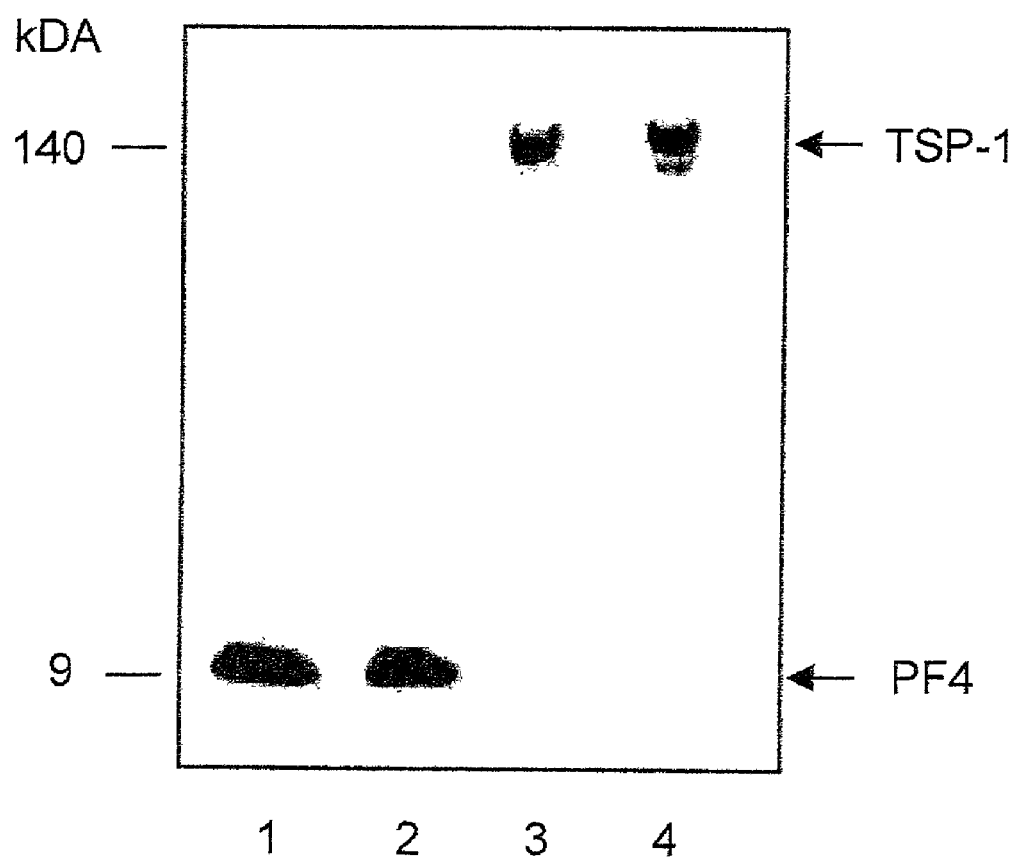
FIG. 2 is a photograph showing the electrophoretic mobility and purity of the isolated protein present in 20 µl samples of two different preparations, prepared according to the methods disclosed herein, of PF4 (Lanes 1–2), and two different preps of TSP-1 (Lanes 3–4) analyzed on 4–15% gradient SDS-PAGE gels stained with Coomassie Blue.

The starting material for the purification of human PF4 and TSP-1, both of which are abundant platelet $\alpha$-granules heparin-binding proteins, was outdated platelet concentrates obtained from the Brigham and Women's Hospital Blood Bank (Boston, Mass.). PF4 has a high affinity for heparin, and requires 1.5 M NaCl before it can be eluted from heparin-Sepharose column (FIG. 1A). In contrast, TSP-1 requires only 0.55 M NaCl for elution from a heparin-Sepharose (FIG. 1A). The platelets were washed, and the supernatant from thrombin-treated platelets was prepared as described previously (Lawler, J., et al., J. Biol. Chem., 260:3762–3772 (1985); Levine, S. P., et al., J. Biol. Chem., 251:324–328 (1985)) with some modifications according to the following protocols:

TSP-1 Isolation:

The supernatant was applied to a column of heparin-Sepharose CL-6B (Pharmacia) at 4° C. Stepwise elution was carried out with 15 mM Tris-HCl (pH 7.6) and 2 mM $CaCl_2$ containing 0.15, 0.25, 0.55, and 2 M NaCl. The fractions from the 0.55 M NaCl peak (e.g., TSP-1 containing fractions) were pooled and passed over an anti-vitronectin antibody column. The flow-through from this column was determined to be free of vitronectin, as measured by Western blotting. Material eluted from the anti-vitronectin antibody column was concentrated by precipitation with 40% (w/v) ammonium sulfate. The sample was resuspended in 15 mM Tris-HCl (pH 7.6), 15 mM NaCl with 2 mM $CaCl_2$ and layered onto linear 10–20% sucrose gradients which were centrifuged at 4° C. in a Beckman SW41 rotor for 16 h at 39,000 rpm (Lawler, J., et al., J. Biol. Chem., 260:3762–3772 (1985)). Fractions from the sucrose gradients containing TSP-1 were stored at −20° C. As shown in FIG. 2, lanes 3 and 4, TSP-1 isolated according to the method described herein produces a preparation comprising TSP-1 which migrates as a single band as determined by SDS-PAGE.

PF4 Isolation:

The fractions from the 2 M NaCl peak of the heparin-Sepharose column were pooled and concentrated by Centriplus Concentrators. Further purification of the concentrated material was accomplished by gel filtration using a Superdex G-75 column equilibrated with 0.15 M NaCl-0.05 M Tris HCl with 0.04% trifluoroacetic acid (TFA) (pH 7.6) buffer. Aliquots of PF4 were stored at −20° C. in 0.04% TFA. As shown in FIG. 2, lanes 1 and 2, PF4 isolated according to the method described herein produces a preparation which migrates as a single band as determined by SDS-PAGE.

Electrophoretic Analysis:

The described procedures for isolating TSP-1 (by heparin-Sepharose affinity chromatography, anti-vitronectin antibody column and sucrose density gradient) and PF4 (by heparin-Sepharose affinity chromatography and gel permeation chromatography) produce proteins that migrate as a single band by SDS-PAGE (FIG. 2). Accordingly, the data FIG. 2 demonstrate that TSP-1 and PF4 each migrate as a single band of apparent molecular mass 180,000 Da and 9,000 Da, respectively.

Example 2

Demonstration of Heparin, TSP-1 and PF4 Complex Formation: Iodination of Heparin and Gel Permeation Chromatography.

In order to determine if PF4, TSP-1 and heparin can interact (e.g., complex) with each other in solution, mixtures comprising $^{125}$I-heparin (4.8×10$^5$ cpm/0.17 U∼4.8×10$^5$ cpm/μg), potentially complexed as PF4/$^{125}$I-heparin, TSP-1/$^{125}$I-heparin or PF4 $^{125}$I-heparin/TSP-1 were applied to Sephadex G200 ($V_o$=16 ml, $V_t$=80 ml) in Tris-buffered saline with 2 mM CaCl$_2$. Elution of $^{125}$I-heparin containing complexes was monitored using a gamma counter. In order to preform heparin binding protein/$^{125}$I-heparin complexes, 2.5 μl of $^{125}$I-heparin was incubated with either 0.5 ml of 40 μg/ml PF4, or with 0.5 ml of 10 μg/ml TSP-1 or with 0.5 ml of 40 μg/ml PF4 and 10 μg/ml TSP-1. Preformed heparin binding protein/$^{125}$I-heparin complexes were incubated 30 min at 4° C. and applied to the column. Heparin was derivatized and iodinated as described previously (San Antonio, J. D., et al., *Biochemistry*, 32:4746–4755 (1993)).

Figure 3:
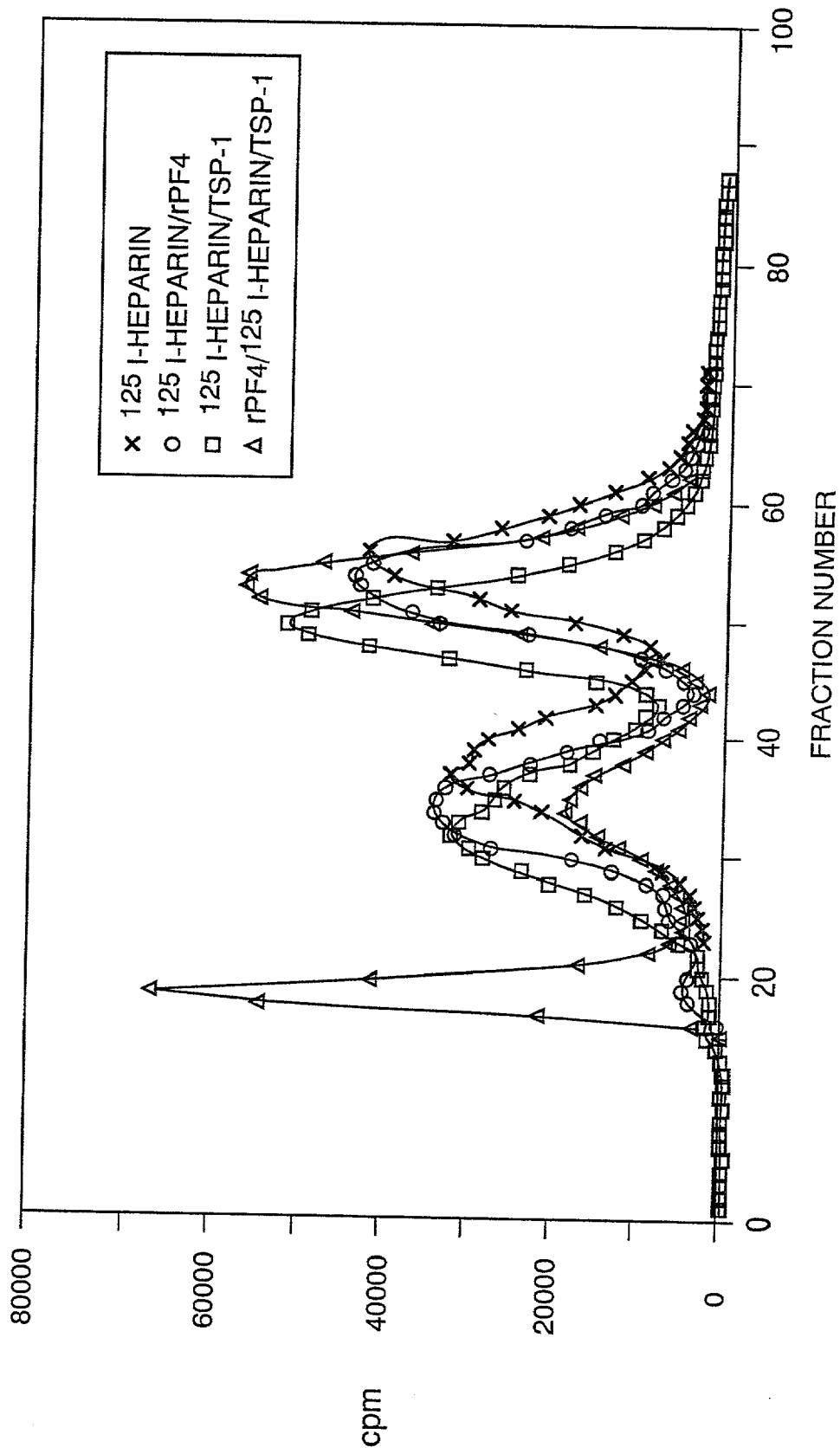
FIG. 3 represents the coelution profiles of various heparin/heparin binding protein complexes eluted from a Sephadex G200 column. Profiles were monitored by using a gamma counter to detect the elution of $^{125}$I-heparin. The complexes comprise heparin bound to either PF4 or TSP-1 (e.g., a binary complex) alone or heparin bound in a ternary complex (PF4/heparin/TSP-1 complex).

Results:

The binding of rPF4, $^{125}$I-heparin and TSP-1 was also examined by gel permeation chromatography in Tris-buffered saline on a Sephadex G200 column. $^{125}$I-heparin is eluted at a $K_{av1}$ of 0.33 (first peak) and a $K_{av2}$ of 0.6 (second peak), assuming the elution of the high and low molecular weight of unfractionated heparin, respectively (FIG. 3). When the rPF4/$^{125}$I-heparin complex is eluted in the absence of TSP-1, the radiolabeled material is eluted at a $K_{av1}$ of 0.28 and a $K_{av2}$ of 0.58 (FIG. 3). When the TSP/$^{125}$I-heparin complex is eluted in the absence of rPF4, the radiolabeled material is eluted at a $K_{av1}$ of 0.25 and a $K_{av2}$ of 0.53 (FIG. 3). The elution position of a major portion of the labeled material was shifted to a $K_{av1}$ of 0.05, $K_{av2}$ of 0.28 and a $K_{av3}$ of 0.58 after the $^{125}$I-heparin was incubated with rPF4 and TSP-1 before application to the gel permeation column. The data presented in FIG. 3, which summarizes the observed shift in elution position of the first peak, indicate that a ternary complex comprising rPF4, heparin and TSP-1 has formed.

Example 3

Optimizing the Ratio of Heparin and Heparin Binding Proteins to Produce Complexes Suitable for the Detection of Antibodies Indicative of HIT.

Binding of HIT antibodies to complexes between heparin and PF4, heparin and TSP-1 or a mixture of heparin, PF4 and TSP-1, was determined by ELISA. Plasma samples from 6 HIT patients were analyzed. PF4/heparin, TSP-1/heparin or PF4/heparin/TSP-1 complexes were preformed by incubating PF4 (1.25 to 40 μg/ml), or TSP-1 (1.25 to 40 μg/ml) or a mixture of PF4 (1.25 to 40 μg/ml) and TSP-1 (1.25 to 40 μg/ml) with heparin (0 to 1 U/ml) in PBS for 30 min at +4° C. The optimal ratios of PF4/heparin, TSP-1/heparin and PF4/heparin/TSP-1 required to produce complexes capable of binding heparin-induced antibodies were determined in preliminary studies. The optimum concentrations used for PF4/heparin ELISA: 20 μg/ml PF4 and 0.03 U/ml heparin; for TSP-1/heparin ELISA: TSP-1 1–5 μg/ml TSP-1 and 0.03 U/ml heparin; and for PF4/heparin/TSP-1 ELISA: 20 μg/ml PF4, 0.03 U/ml heparin and 1 μg/ml TSP-1.

Figure 4A:
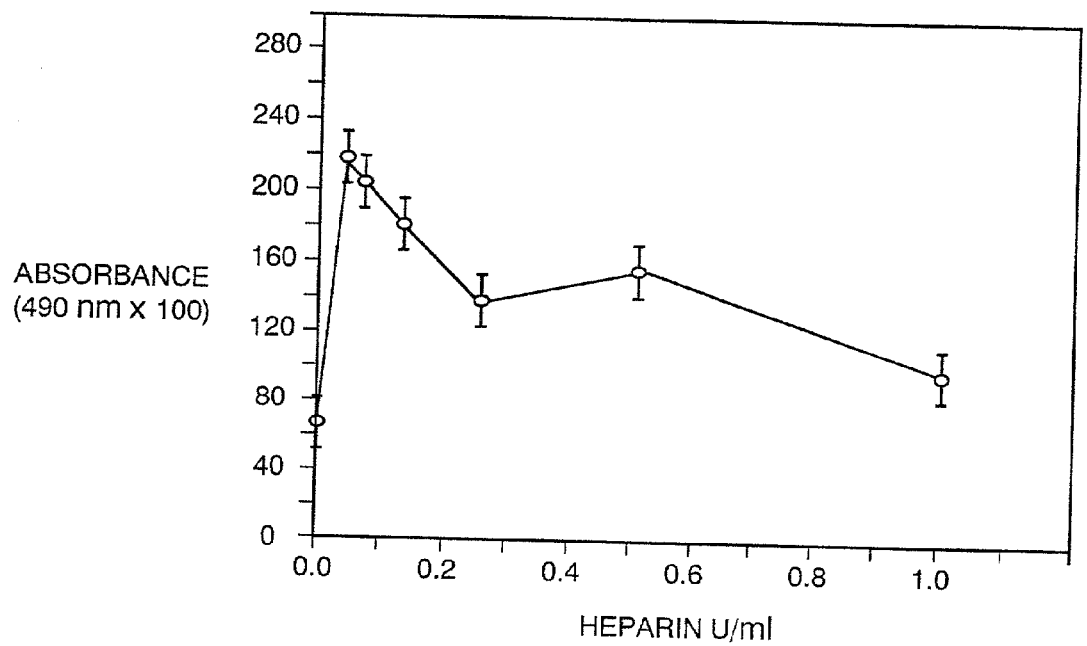
FIG. 4A is a graph of ELISA data (measuring $OD_{490}$ of the complexes) demonstrating the binding profile of immunoglobulin present in six HIT patient plasma samples to PF4/heparin complexes immobilized on a solid phase comprising heparin/heparin binding protein complexes preformulated at different ratios. The graph illustrates the effects of varying the heparin concentration (0–1 U/ml) admixed with a constant amount of PF4 (20 µg/ml) on the binding of HIT patient antibodies.
Figure 4B:
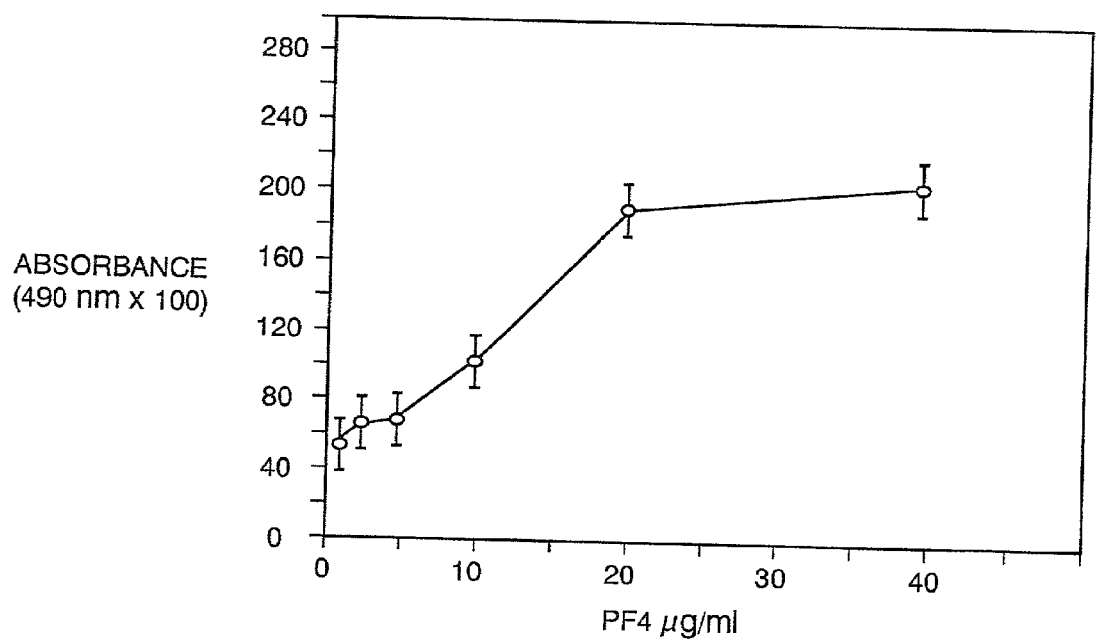
FIG. 4B is a graph of ELISA data (measuring $OD_{490}$ of the complexes) demonstrating the binding profile of immunoglobulin present in six HIT patient plasma samples to PF4/heparin complexes immobilized on a solid phase comprising heparin/heparin binding protein complexes preformulated at different ratios. The graph illustrates the effects of varying the PF4 concentration (1.25–40 µg/ml) admixed with a constant amount of heparin (0.03 U/ml) on the binding of HIT patient antibodies. Results are expressed as the mean±SEM.

PF4/Heparin Results:

Complexes formed in mixtures containing 20 μg/ml PF4 and heparin at concentrations ranging from 0 to 1 U/ml were immobilized in duplicate in the wells of microtiter plate and used as an immunoadsorbent for immunoglobulin present in HIT patient plasma samples. FIGS. 4A and 4B summarize ELISA data obtained using 6 HIT patient plasma samples. FIG. 4A indicates that HIT patient immunoglobulin readily binds to PF4/heparin complexes preformed in a mixture comprising 20 μg/ml PF4 and 0.03 U/ml heparin. Using various concentrations of PF4 (1.25 to 40 μg/ml) and 0.03 U/ml heparin, Applicants confirmed that 20 μg/ml PF4 was required to obtain the optimal binding of HIT patient's plasma antibodies under these conditions (FIG. 4B).

TSP-1/Heparin Results

Figure 5A:
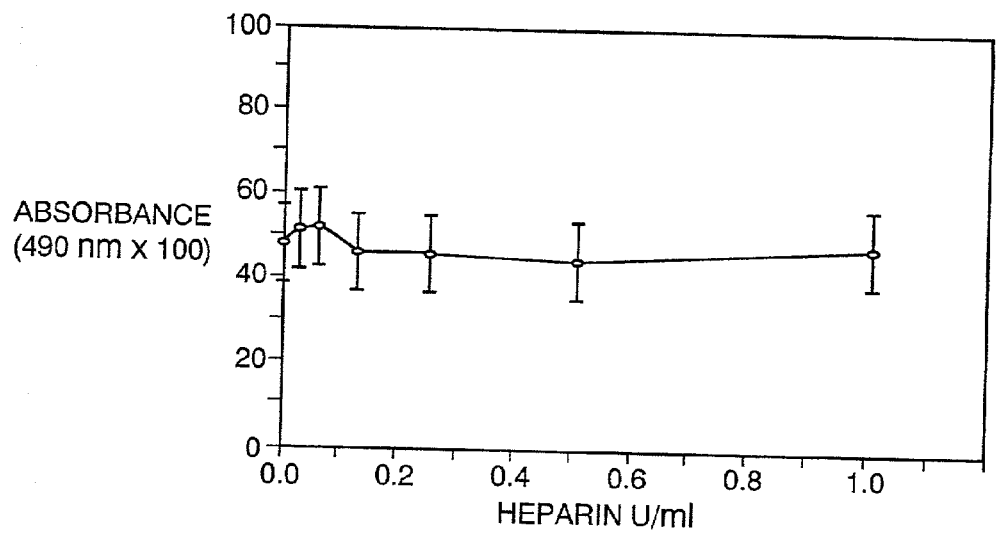
FIGS. 5A–5C present a set of three graphs illustrating ELISA data resulting from a determination of the binding profile of immunoglobulin present in six HIT patient plasma samples to preformulated TSP-1/heparin complexes immobilized on a solid phase at different ratios.
Figure 5B:
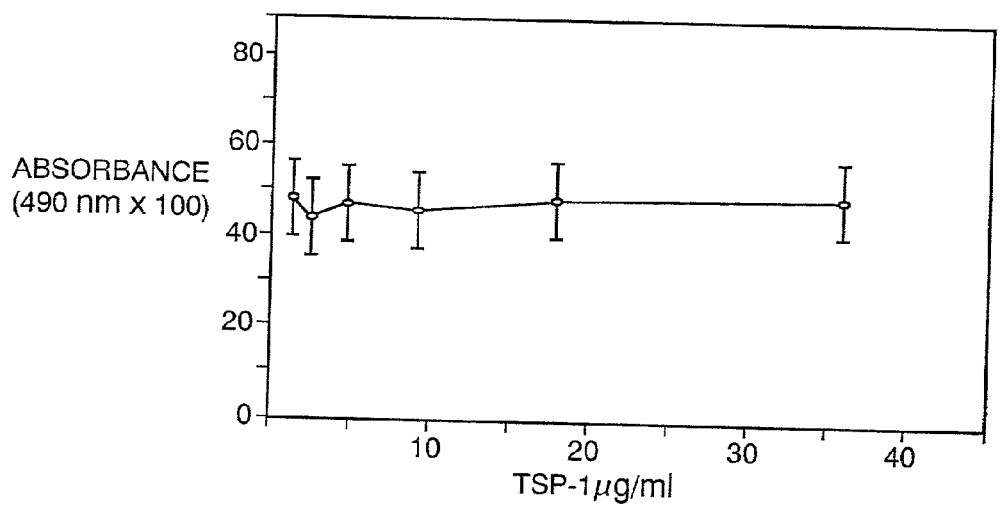
Figure 5C:
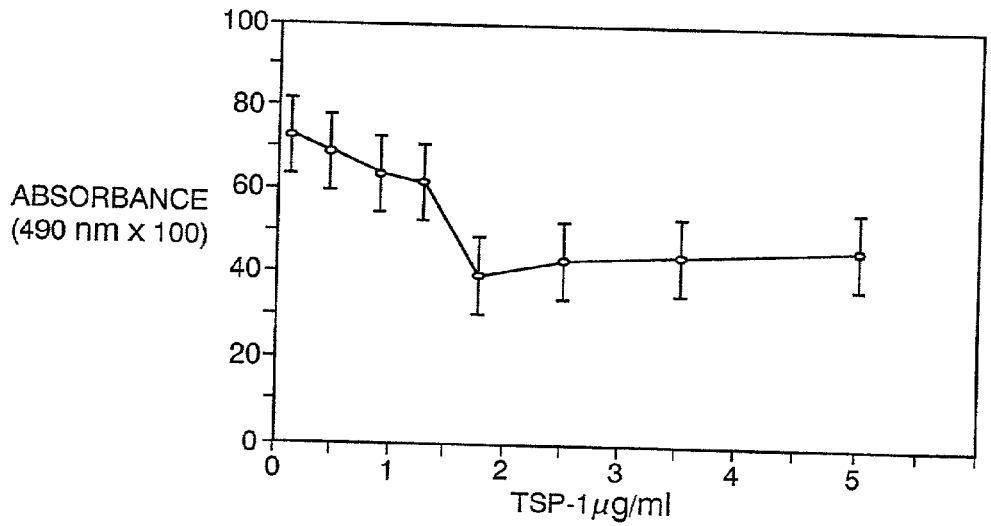

Applicants further investigated whether the immunoglobulin present in HIT patient's plasma cross-reacts with TSP-1/heparin complexes. As shown in FIG. 5A, there are no significant differences in the binding profile obtained using 20 μg/ml TSP-1 and variable concentrations of heparin (0 to 1 U/ml). Furthermore, increasing the TSP-1 concentration from 1.25 to 40 μg/ml and using 0.33 U/ml heparin did not mediate any significant difference in the binding (FIG. 5B) profile. By contrast, when using various concentrations of TSP-1 starting from 0.1 μg/ml to 5 μg/ml and a fixed concentration of heparin (0.03 U/ml), 0.5 to 1 μg/ml TSP-1 was required to obtain the optimal binding of HIT patient's plasma antibodies (FIG. 5C).

Figure 6:
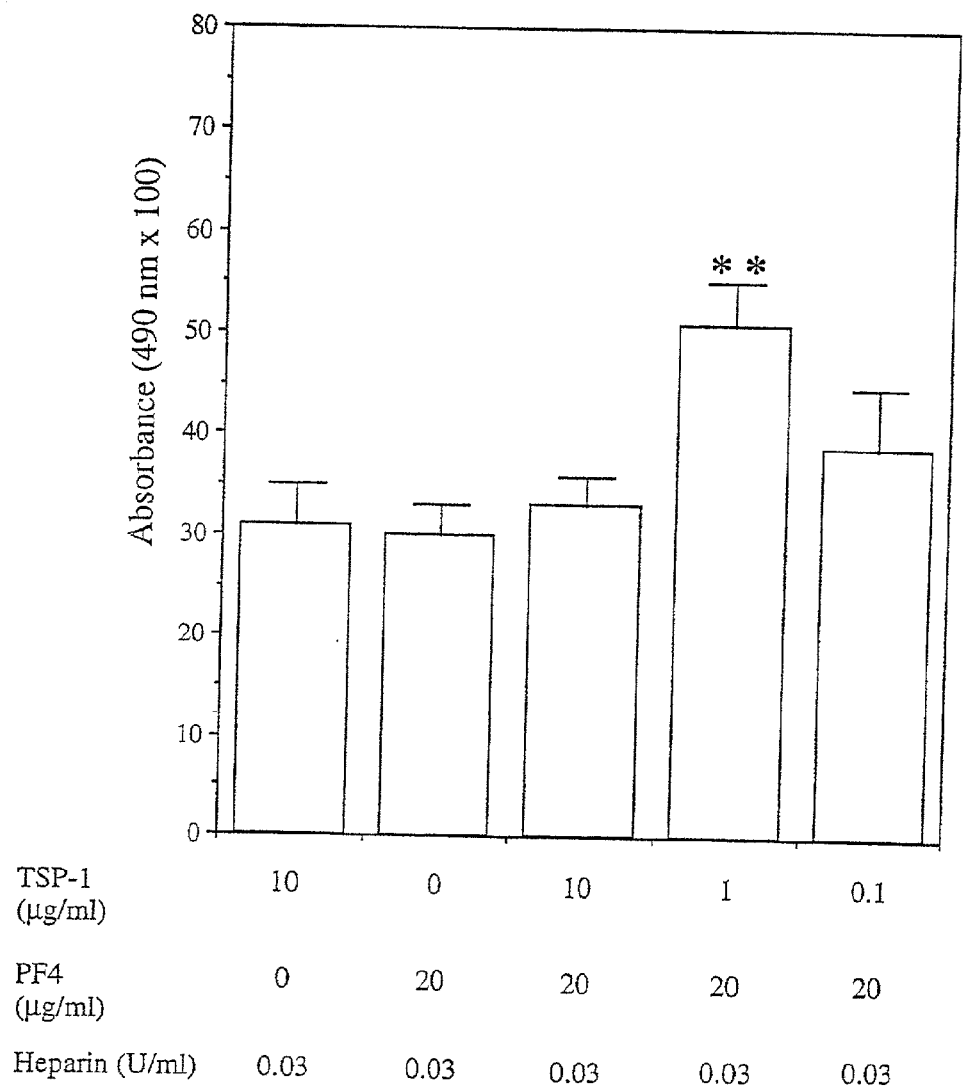
FIG. 6 is a graph illustrating ELISA data resulting from a determination of the binding profile of immunoglobulin present in five HIT patient plasma samples to PF4/heparin, TSP-1/heparin and PF4/heparin/TSP-1 complexes at different ratios of the components of the antigenic complex. Results are expressed as the mean±SEM.

The presence of antibodies against PF4/heparin and TSP-1/heparin complexes in patients with HIT suggests that the antibodies are different immunoglobulin molecules directed against distinct epitopes on PF4/heparin and TSP-1/heparin complexes. This concept is supported by the data in Table 2 and FIG. 6, showing increased values for absorbance and sensitivity when the PF4/heparin/TSP-1 complexes are used for a target for antibody binding, rather than PF4/heparin or TSP-1/heparin complexes.

PF4/Heparin/TSP-1 Results:

The cross-reactivity of HIT patient plasma with various complexes was also determined using the ELISA embodiment of the assay disclosed herein. FIG. 6 illustrates that HIT patient's plasma antibodies readily cross-react with a PF4/heparin/TSP-1 ternary antigen complex, particularly when the complex was preformed in a mixture comprising 20 μg/ml PF4, 1 μg/ml TSP-1 and 0.03 U/ml heparin, which was determined to be the optimal ratio for this particular set of ternary complex components.

Example 4

ELISA Comparison

General Description of the PF4/heparin, TSP-1/heparin and PF4/heparin/TSP-1 ELISA Microtiter 96-well plates (activated or not activated with maleic anhydride) were coated overnight at 4° C. with 100 μl of PF4/heparin, TSP-1/heparin, or PF4/heparin/TSP-1 complexes preformed at empirically determined optimal molar ratios. Unreactive sites were subsequently blocked by adding 10% (wt/vol) goat serum in PBS for 2 hours at +4° C. and the wells were washed three times with PBS-T.

Patient, or negative control normal plasma or serum samples, were diluted 1:50 in PBS-10% goat serum (200 μl/well) and were added to duplicated assay wells and maintained at room temperature for 1 hour. After three washes with PBS-T, the presence of bound ternary complex-reactive human-IgG, -IgA and/or -IgM was quantified by adding peroxidase conjugated goat anti-human-IgG, IgA, IgM (5 μg/ml, 200 μl/well), followed by incubation for 1 hour at room temperature. After another three washes with PBS-T, 200 μl OPD (0.8 mg/ml) substrate and $H_2O_2$ (0.2%) was added to the wells for 5 min. Fifty microliters of $H_2SO_4$ (3 M) were added to stop color development, and the absorbance at 490 nm was determined. A positive result was defined as one that was greater than the average absorbance observed for the negative control sample plus 3 standard deviations. Absorbance values below that cutoff were considered to be negative.

Commercial rPF4/Heparin ELISA Kit.

The assay was performed according to the manufacturer's instructions. Briefly, recombinant PF4/heparin coated microtiter wells were incubated in duplicate with 1/101 dilutions of plasma for 1 hour, washed, then incubated with peroxidase conjugated secondary antibody directed against human IgG, IgM and IgA. Following another wash, OPD and $H_2O_2$ were added for 5 min before the color development was stopped by the addition of $H_2SO_2$. Absorbance at 490 nm was measured using a microtiter plate reader. The manufacturer's instructions stated that absorbance greater than 0.5 should be regarded as positive.

Comparison:

Applicants determined the sensitivity and specificity of PF4/heparin, TSP-1/heparin and PF4/heparin/TSP-1 complex-reactive ELISA assays using two different types of solid phase support materials: polystyrene and maleic anhydride activated polystyrene. Applicants attribute the increased absorbance values obtained using Reacti-Bind™ maleic anhydride activated polystyrene ELISA plates compared to nonactivated polystyrene plates to non-specific binding of some antibodies to the wells pre-activated with maleic anhydride. Polystyrene plates were used for coating protein/heparin or PF4/heparin/TSP-1 complexes to compare the sensitivity and specificity of the Stago Diagnostica rPF4/heparin ELISA kit and the ELISA described herein.

Results:

According to the results of the platelet aggregation test (PAT) and the commercial rPF4/heparin ELISA, Applicants stratified the 36 patients with suspected HIT into four groups, based on the binding profile and observed degree of platelet aggregation observed in each sample. As shown in Table 1, nine of 36 patients were positive with the PAT and the commercial ELISA, 9 of 36 were positive with the PAT but negative with the commercial ELISA, 9 of 36 were negative with the PAT but positive with the commercial ELISA and 9 of 36 were negative with both the PAT and the commercial ELISA.

TABLE 1

Results of the platelet aggregation test and the commercial rPF4/heparin assay in 36 patients with suspected HIT

| Patient group | I | II | III | IV |
|---|---|---|---|---|
| n | 9 | 9 | 9 | 9 |
| Platelet aggregation test | + | + | − | − |
| Commercial ELISA kit | + | − | + | − |

According to the manufacturer's instructions for the commercial rPF4/heparin assay, a positive plasma has an absorbance higher than 0.5 and a negative plasma has an absorbance less than 0.5. According to Applicants' disclosed ternary complex ELISA protocol, a positive plasma has an average absorbance higher than 0.14. The base line for Applicants' PF4 (20 μg/ml)/heparin (0.03 U/ml) assay is 0.11. Table 2 summarizes the sensitivity and specificity of the disclosed PF4/heparin, TSP-1/heparin and PF4/heparin/TSP-1 ELISA assays in comparison with that of the commercially available rPF4/heparin assay and the standard PAT.

TABLE 2

Comparison of the sensitivity and specificity of PF4/heparin, TSP-1/heparin and PF4/heparin/TSP-1 ELISAs as described herein with the commercially available rPF4/heparin kit and the PAT for 36 HIT patients

|  | Sensitivity | Specificity |
|---|---|---|
| Commercial rPF4/heparin ELISA | 50% | 90% |
| Platelet aggregation test | 50% | 100% |
| Our PF4-1/heparin | 61% | 100% |
| TSP-1/heparin | 25% | 100% |
| PF4/heparinlTSP-1 | 92% | 100% |

Figure 7A:
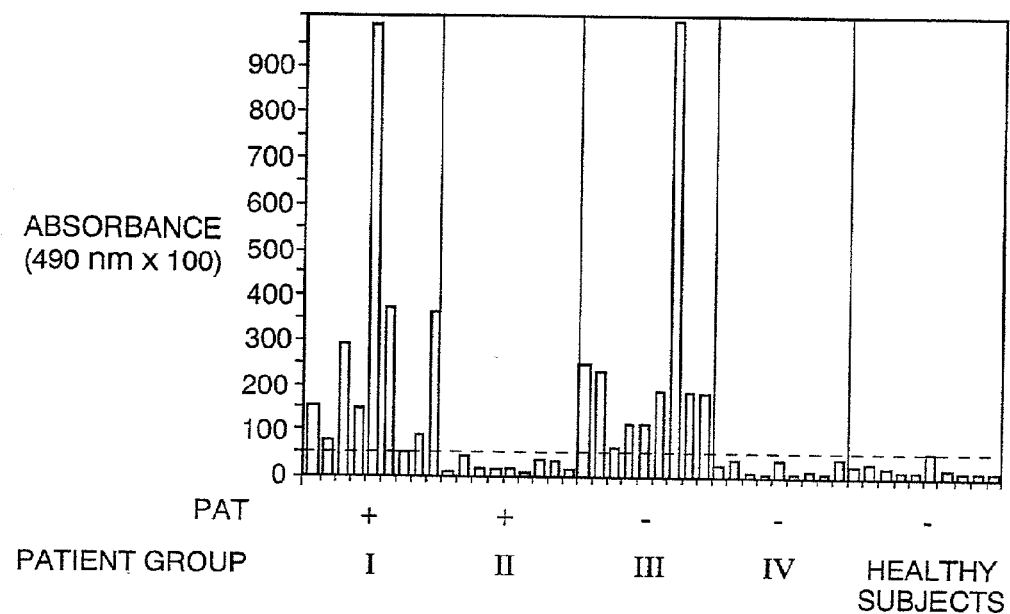
FIG. 7A summarizes the results obtained with the commercial ELISA kit which employs recombinant PF4/heparin complexes.
Figure 7B:
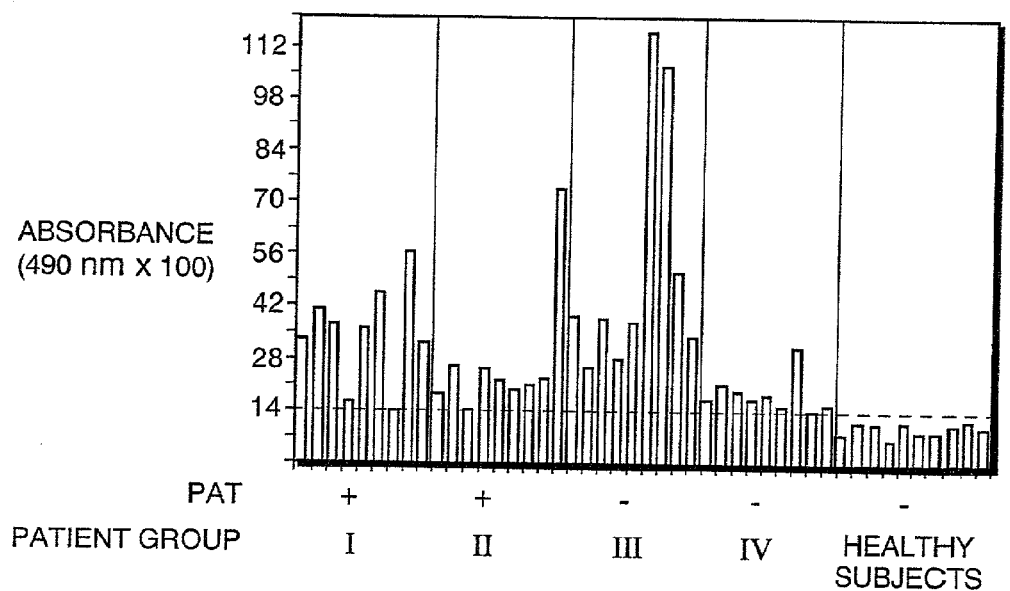
FIG. 7B summarizes the results obtained for the same samples analyzed with the PF4/heparin/TSP-1 method disclosed herein. Samples are considered positive if the absorbance is greater than three standard deviations above the mean of the normal controls (dashed line).

Results:

The data presented in FIG. 7, and summarized in Table 2, indicate that with the commercial ELISA kit, 18 of 36 (50%) of the HIT patients tested positive, and 18 of 36 (50%) tested negative, which is in agreement with the data presented in Table 1. In addition, 9 of 10 (90%) of the normal samples produced negative results, in a test of the specificity of the assay. Thus, using this set of samples, the commercially available ELISA kit produced a false negative rate of 50% and a 10% false positive rate. In comparison, Applicants' PF4/heparin ELISA protocol detected PF4/heparin reactive immunoglobulin in 61% of the plasma samples. The data in Table 2 further demonstrate that 25% (9/36) of the HIT patient plasma samples also comprise TSP-1/heparin reactive immunoglobulin.

The data presented in FIG. 7 and summarized in Table 2 indicate the superior sensitivity of Applicants PF4/heparin/TSP-1 ELISA format, which detects ternary complex reactive immunoglobulin in 92% of the HIT patient plasma samples, as compared to both the commercial ELISA Kit (50% sensitivity) and the traditional PAT (50% sensitivity).

As shown in Table 2, the specificity of all three of Applicants' ELISA protocols was determined to be 100%. This was determined by assessing the binding of the ten negative control samples (e.g., normal plasma obtained from healthy donors) to either a PF4/heparin complex, a TSP-1/heparin complex, or a PF4/heparin/TSP-1 ternary complex coated solid phase. The data summarized in Table 2 further indicate that the specificity of the PAT assay, as performed by Applicants was also 100%, because all ten plasma samples obtained from healthy subjects resulted in absorbance values which were negative.

The relevant portions of all references (e.g., journal articles, books, published patent applications and patents, etc.) cited herein are hereby incorporated by reference.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A kit for detecting the presence of immunoglobulin reactive with a platelet factor 4/heparin/thrombospondin-1 antigen complex, comprising:
   a solid phase support material on which a platelet factor 4/heparin/thrombospondin-1 ternary complex has been immobilized; a buffered medium comprising isolated human TSP-1;
   a wash medium formulated to reduce nonspecific binding;
   at least one anti-human immunoglobulin reactive reagent detectably labeled with a reporter molecule, and having a specificity for at least one isotype of human immunoglobulin;
   a standardized positive control comprising known amounts of ternary complex reactive antibody;
   a negative control sample; and
   a diluent reagent.

2. A kit for detecting the presence of immunoglobulin reactive with a platelet factor 4/heparinlthrombospondin-1 antigen complex, comprising:
   a solid phase support material on which a platelet factor 4/heparin/thrombospondin-1 ternary complex has been immobilized;
   a wash medium formulated to reduce nonspecific binding;
   at least one anti-human immunoglobulin reactive reagent detectably labeled with a reporter molecule, and having a specificity for at least one isotype of human immunoglobulin;
   a standardized positive control comprising known amounts of ternary complex reactive antibody;
   a negative control sample; and
   a diluent reagent.

* * * * *